Figure 1:
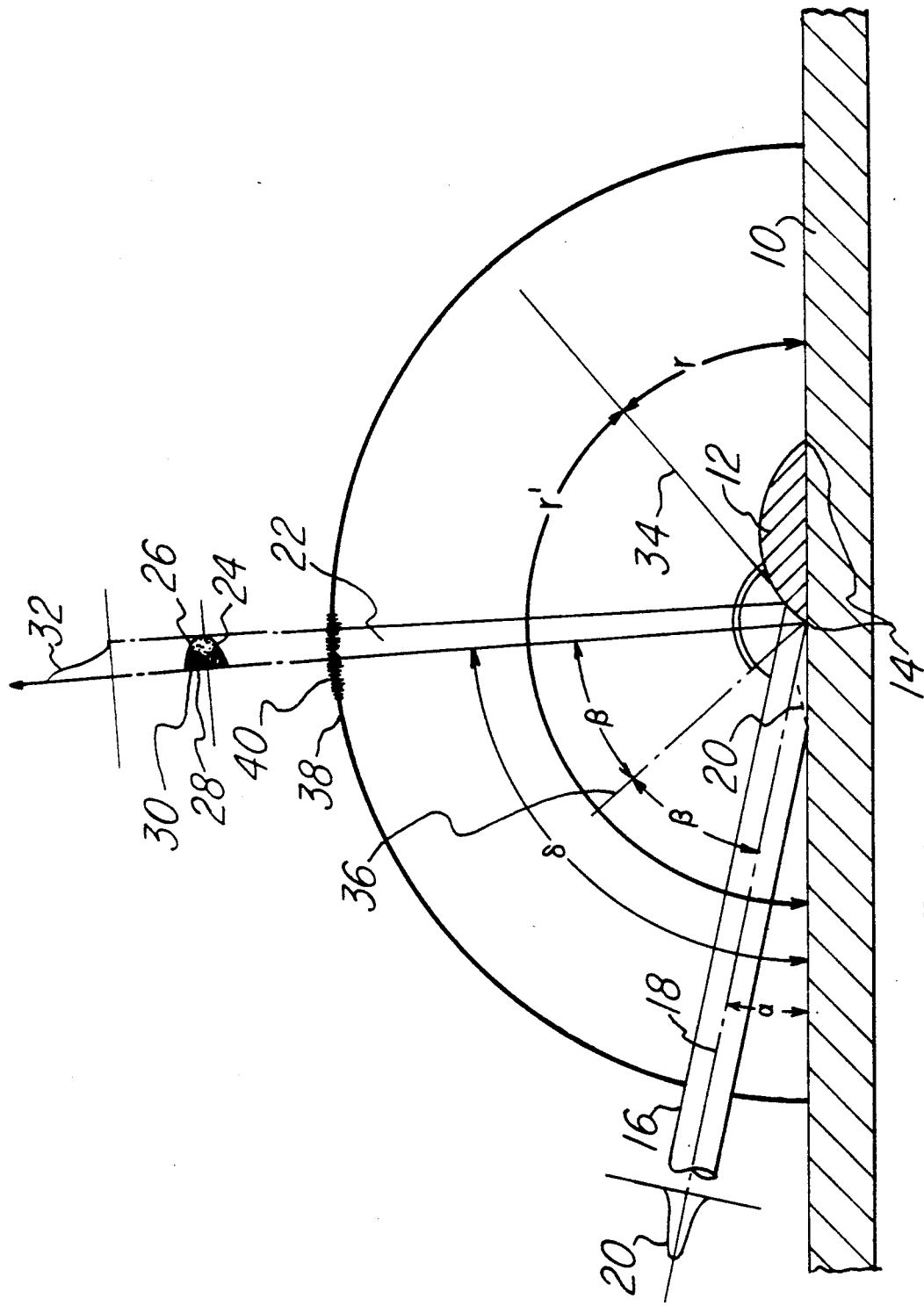

United States Patent [19]

Schneider et al.

[11] Patent Number: 5,080,484
[45] Date of Patent: Jan. 14, 1992

[54] METHOD OF MEASURING THE CONTACT ANGLE OF WETTING LIQUID ON A SOLID SURFACE

[75] Inventors: Helmut Schneider, Fischbachau; Helmut Rinck, Langenbach, both of Fed. Rep. of Germany

[73] Assignee: Texas Instruments Deutschland GmbH, Fed. Rep. of Germany

[21] Appl. No.: 344,735

[22] Filed: Apr. 28, 1989

[30] Foreign Application Priority Data

Apr. 29, 1988 [DE] Fed. Rep. of Germany ....... 3814662

[51] Int. Cl.$^5$ .............................................. G01B 11/26
[52] U.S. Cl. ...................................... 356/154; 356/138
[58] Field of Search ........................ 356/138, 150, 154; 73/64.4

[56] References Cited

U.S. PATENT DOCUMENTS 3,405,578 10/1968 Persson ................................ 356/138
4,688,938 8/1987 Demoulin et al. .................. 356/138

FOREIGN PATENT DOCUMENTS 2053390 5/1972 Fed. Rep. of Germany .
3542928 6/1986 Fed. Rep. of Germany .
130607 10/1981 Japan ................................... 356/138
1265549 10/1986 U.S.S.R. .............................. 73/64.4

Primary Examiner—Richard A. Rosenberger
Attorney, Agent, or Firm—William E. Hiller; N. Rhys Merrett; Melvin Sharp

[57] ABSTRACT

The invention relates to a method of measuring the contact angle of wetting liquids on a solid surface with which a high measuring accuracy and better reproduceability of the measurement results is achieved. The method resides in that a laser beam is directed onto the interface line between the liquid and the plane solid surface in such a manner that a first part of the laser beam is reflected by the solid surface and a second part by the liquid surface. The second partial beam is used as measuring beam by determining the angle ($\delta$) made between the measuring beam and the solid surface, said angle being in a fixed geometrical relationship to the contact angle (r). The contact angles which can be determined very accurately with this measuring method provide information on wetting properties of materials, the exact knowledge of which is of great significance for example for semiconductor fabrication.

7 Claims, 3 Drawing Sheets

METHOD OF MEASURING THE CONTACT ANGLE OF WETTING LIQUID ON A SOLID SURFACE

The invention relates to a method of measuring the contact angle of wetting liquids on a solid surface.

The contact angle r is a measurement of the wetting properties of liquids on solid surfaces. Completely wetting liquids have a contact angle r of 0°. Liquids having a contact angle 0°<r<90° are referred to as wetting and liquids having a contact angle greater than 90° are referred to as poorly wetting or non-wetting.

The exact determination of wetting properties is for example of great significance in semiconductor fabrication. When the wetting behaviour of liquids on wafer surfaces is known conclusions can be drawn on further physical and/or chemical boundary effects on the surface. This leads to a deeper understanding of the processes taking place during the fabrication.

In contact angle measuring methods according to the prior art the boundary line region between the liquid and the solid surface is optically magnified. For this purpose, for example, microscopes or measuring eyepieces are used. The contact angle is then determined in that a tangent is laid to the liquid surface curved to a greater or lesser extent and intersects the boundary or interface line, the angle between this optically construed tangent and the solid surface being determined. However, the path of the tangent can only be determined approximately and this impairs the accuracy and reproduceability of the contact angle measurement. The measurement is relatively time-consuming and the measurement result is only subjective because the laying of the tangent depends decisively on the person performing the measurement.

The resulting measurement inaccuracy is particularly unacceptable in the determination of wetting properties in the field of semiconductor fabrication.

The problem therefore arises of making available a measuring method for determining the contact angle which has greater measuring accuracy and better reproduceability and can be rapidly and easily carried out.

The solution of this problem is set forth in the characterizing clause of claim 1. This solution is based on the recognition that the angle $\delta$ between the plane of the solid surface and the partial beam reflected from the liquid surface is in a fixed geometrical relationship to the contact angle r so that with determination of the angle $\delta$ the contact angle r is simultaneously measured.

The measuring method according to claim 1 has the advantage that it is independent of the person carrying out the method and is thus objective. It can be carried out rapidly and easily because complicated estimations of the tangent path are no longer necessary. Since the method is no longer dependent on optical magnifying instruments, for example measuring eyepieces, measurement over a longer distance is readily possible so that even during the measurement the measured object can be exposed in reaction containers to high temperatures and/or pressures. The measurement apparatus necessary for carrying out the measuring method can be kept simple and thus economical because only small precision-mechanical components and not so much optical components are needed. Because of these advantages the measuring method is particularly suitable for contact angle determination in semiconductor production.

A particularly advantageous embodiment of the measuring method is apparent from claims 2 to 4. If the centre line of the laser beam intersects the interface line between the liquid and the solid surface then the partial beam reflected by the liquid surface has a sharp contrast line. Using this contrast line the angle $\delta$ can be determined with very high accuracy. In accordance with claim 3 the angle determination can be carried out directly by reading the value from a graduated measuring window on which in accordance with claim 4 the contact angle r corresponding to the respective angle $\delta$ can be read off directly.

The embodiment according to claim 5 has the advantage that the partial beam reflected by the liquid surface before emerging into the surroundings is attenuated in its intensity to such an extent that the method can be carried out without endangering the health of the person conducting the measurement.

In a further advantageous development of the contact angle measuring method in accordance with claim 6 for adjusting the measuring beam the incidence angle $\alpha$ of the laser beam is kept constant and only the solid surface with the liquid disposed thereon displaced in the x-y direction. A measuring apparatus for carrying out the method according to this further development can be made in particularly simple and economical manner.

Figure 2:
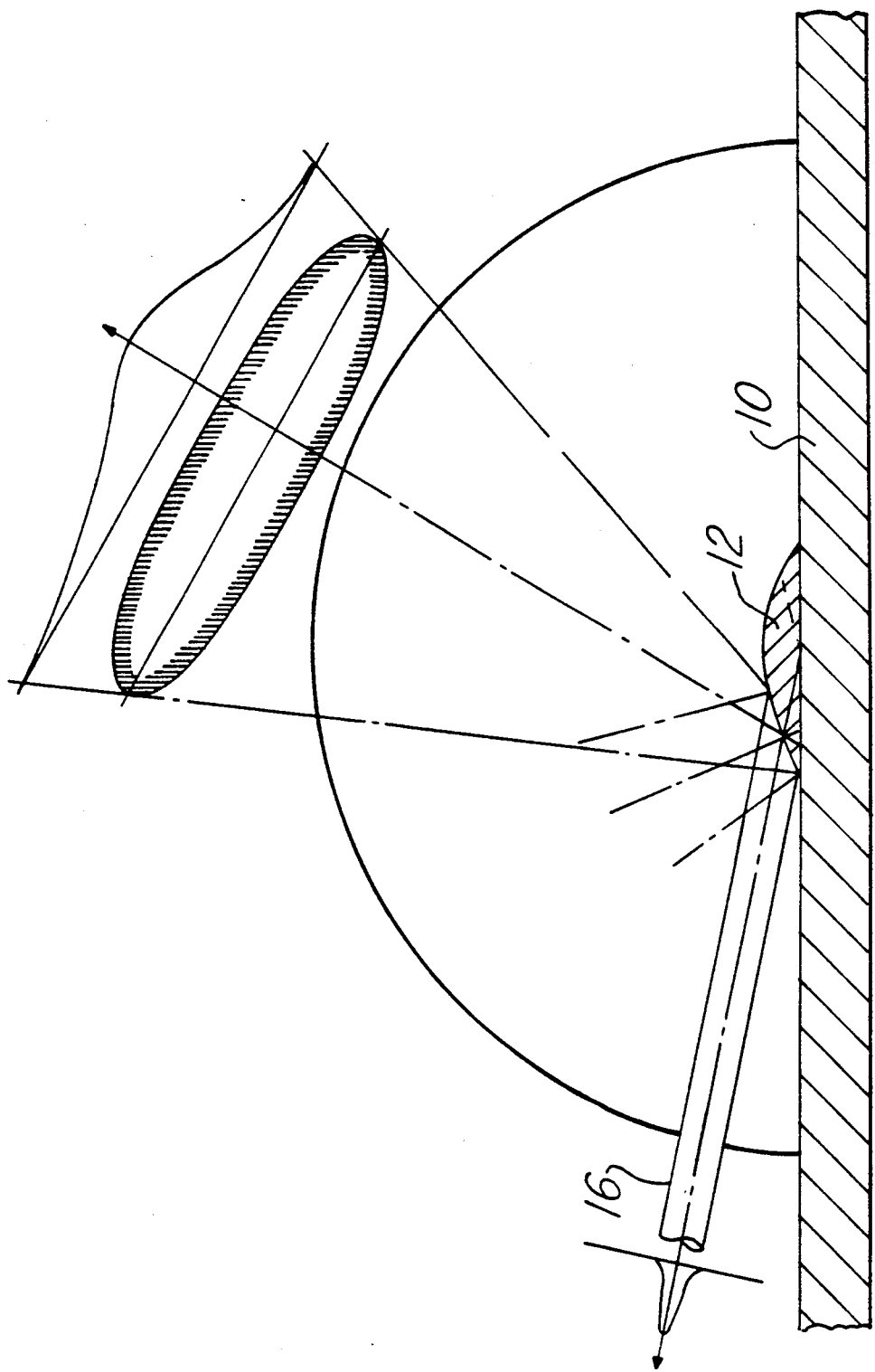
Figure 3:
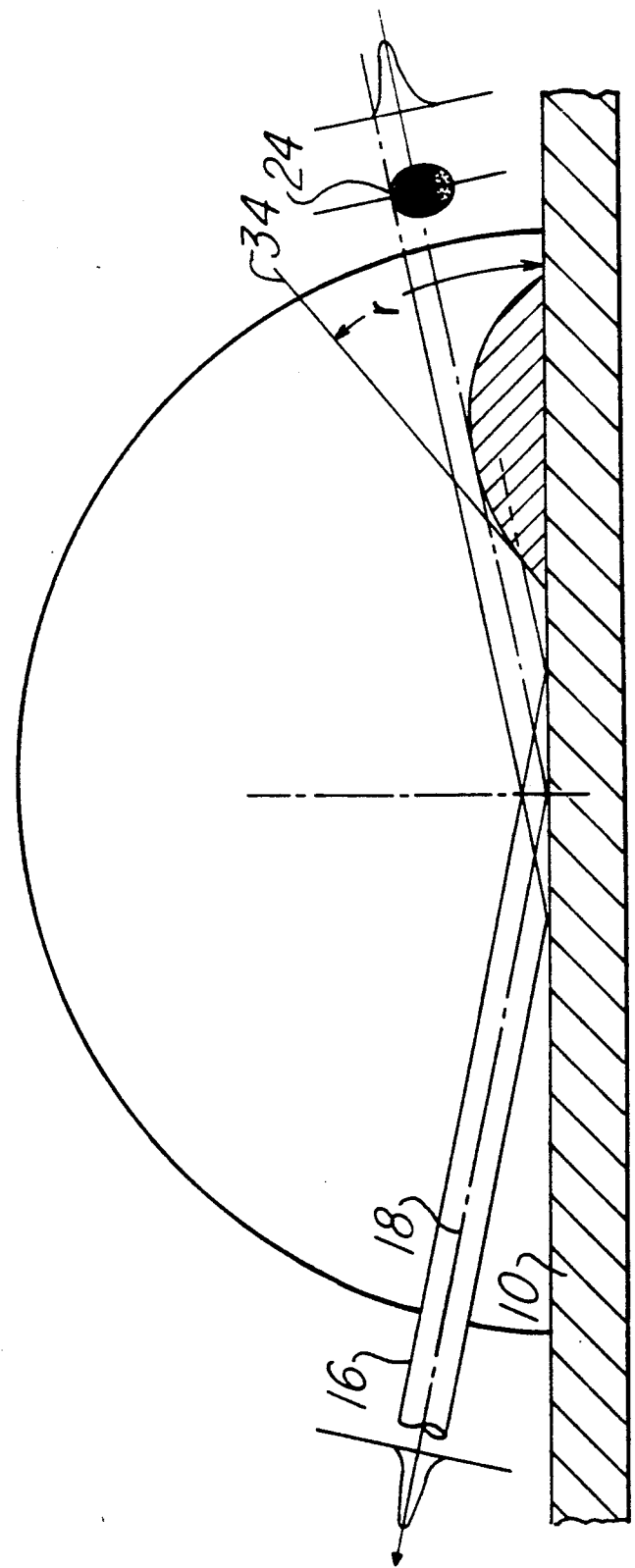

Further details, features and advantages of the invention will be apparent from the following description of the embodiment of the measuring method explained by way of example with the aid of the drawings, wherein FIG. 1 is a schematic illustration of a measuring arrangement for carrying out the measuring method according to the invention at the instant of the contact angle measurement;

FIG. 2 is a schematic illustration of a measuring arrangement for carrying out the measuring method according to the invention in a first operating position in which no measurement is possible and FIG. 3 is a schematic illustration of a measuring arrangement for carrying out the measuring method according to the invention in a further operating position in which no measurement is possible.

Arranged on the surface of the plane sample 10 illustrated in FIG. 1, for example a silicon wafer specimen, is a liquid drop 12 of a wetting liquid, for example water as test liquid. The convexly curved drop forms with the surface of the specimen 10 a boundary or interface line 14. By displacing the specimen 10 by means of the x-y displacement device not illustrated in FIG. 1 a laser beam 16 incident at a constant angle $\alpha$ to the surface of the specimen is aligned so that the symmetry axis 18 of the laser beam 16 intersects the interface or boundary line 14. The diagram designated by the reference number 20 in FIG. 1 shows the intensity distribution of the laser beam 16 plotted against the beam diameter, said distribution having the form of a Gaussian distribution with a maximum lying on the symmetry axis 18 of the beam. In the correct measurement setting illustrated in FIG. 1 the laser beam region with the maximum intensity thus intersects the interface line 14.

The radiation source used is a continuously operated 1 mW He-Ne laser (TEM-00-mode) having a beam diameter of 0.5 mm and a beam spread of 0.1 mrad. The wavelength of the beam generated by the He-Ne laser is 632.8 nm. The measuring method is however not restricted to the use of He-Ne lasers. Fundamentally, any coherent radiation source emitting sharply bundled and strictly parallel light beams is suitable. For example, in cases where the substance to be investigated absorbs the wavelength of the He-Ne laser beam laser radiation of another wavelength is to be used.

In the setting of the laser beam 16 shown in FIG. 1 said beam is divided into two partial beams 20 and 22 arising by reflection. The first partial beam 20 is formed by reflection at the surface of the specimen 10 and is of no significance to the contact angle measurement. The second partial beam 22 is formed at the interface due to an interface reflection caused by the jump of the refractive index between gas and liquid. Due to the convex arching of the liquid drop the reflected partial beam 22 diverges more than the laser beam 16 and consequently its image 24 appears widened compared with the beam. The beam image 24 shown in FIG. 1 exhibits a brighter region 26 and a darker region 28 which is bordered on one side by a pronounced contrast line 30. As apparent from diagram 32 of the intensity distribution of the radiation in the reflected partial beam 22, the contrast line 30 coincides with the intensity maximum. This is true however only in the case illustrated in FIG. 1 in which the symmetry axis 18 of the laser beam 16 meets the interface line 14.

The reflected partial beam 22 serves as measuring beam. An angle $\delta$ is formed between the specimen surface and the interface region of the measuring beam 22 corresponding to the beam image 24 and originating from the interface line 14. Said angle is in a fixed geometrical relationship to the contact angle r defined by the tangent 34.

Assuming a constant angle $\alpha$ of incidence of the laser beam 16 and deducting therefrom the angle $\delta$, there remains a residual angle of $2\beta$ having a bisector 36 extending perpendicularly to the tangent 34. This means:

$\alpha = \text{const.}; \delta = \alpha + 2\beta \text{ or } \beta = (\delta - \alpha)/2$ $\alpha + \beta + 90° = r'; r = 180° - r'$ thus: $r = 90° - \alpha - \beta$ and therefore: $r = (90° - \alpha/2) - \delta/2$ The measuring beam 22 is imaged on a measuring window provided with a measuring scale 38. On the measuring scale 38 the angle $\delta$ can be entered or advantageously directly the contact angle r to be measured if the laser beam is directed onto the specimen with the angle $\alpha = \text{const.}$ for all measurements to be made. The contact angle r is read off at the point 40 at which the contrast line 30 is formed.

The measuring window is made from a material which attenuates the measuring beam 22 image thereon in its intensity so that there is no danger to the health of the person making the measurement.

The setting of the laser beam 16 illustrated in FIG. 2 does not permit measurement of the contact angle. In this case the entire laser beam 16 is incident on the surface of the liquid drop. The reflected beam is greatly widened and does not have the sharply imageable contrast line 30 necessary for determining the angle $\delta$.

Measurement of the contact angle is also not possible with an alignment of the laser beam 16 with respect to the drop 12 as illustrated in FIG. 3. The entire laser beam 16 is incident at the angle $\alpha$ on the specimen surface and is reflected therefrom at the angle $\alpha$ as well. The image 24 of this reflected beam also does not exhibit a sharp contrast line 30.

The occurrence of the sharp constrast line 30 is thus simultaneously a check of whether the laser beam 14 is positioned correctly for measuring the contact angle r.

The measuring method according to the invention permits a highly accurate rapid and easily conducted contact angle measurement. With the aid of the results determinable with this measuring method detailed knowledge can be obtained for solving various coating problems as occur in particular in semiconductor fabrication. For example, a qualitative investigation of extremely thin films down to monomolecular films is possible.

We claim:

1. A method of measuring the contact angle of wetting liquids on a solid surface, said method comprising the steps of:

directing a laser beam substantially non-vertically onto a portion of the interface line between a liquid drop and a plane solid surface on which the liquid drop is disposed to position a portion of the laser beam on the liquid drop and another portion of the laser beam on the plane solid surface;

reflecting a partial beam of the laser beam by the surface of the liquid drop from the portion of the laser beam positioned thereon;

detecting the angle $\delta$ between the reflected partial beam of the laser beam as reflected by the surface of the liquid drop and the plane solid surface; and determining the contact angle r in response to the detected angle $\delta$ in accordance with a fixed geometrical relation to the detected angle $\delta$.

2. A method of measuring the contact angle as set forth in claim 1, further including aligning the laser beam with respect to the liquid drop and the plane solid surface on which the liquid drop is disposed so that the symmetry axis of the laser beam intersects the interface line between the liquid drop and the plane solid surface in directing the laser beam onto the interface line between the liquid drop and the plane solid surface.

3. A method of measuring the contact angle as set forth in claim 2, further including forming an image of the reflected partial beam of the laser beam as reflected by the surface of the liquid drop on a graduated measuring window providing a scale; and the detection of the angle $\delta$ between the reflected partial beam of the laser beam as reflected by the surface of the liquid drop and the plane solid surface being accomplished by reading off the angle $\delta$ at a point on the scale provided by the graduated measuring window at which the image of the reflected partial beam of the laser beam has a line of maximum contrast.

4. A method of measuring the contact angle as set forth in claim 3, wherein the contact angle r is determined by reading the measurement of the contact angle r directly from the scale provided by the graduated measuring window.

5. A method of measuring the contact angle as set forth in claim 3, further including attenuating the intensity of the reflected partial beam of the laser beam as reflected by the surface of the liquid drop to a lower magnitude of an extent not injurious to health in response to the passage of the reflected partial beam through the graduated measuring window.

6. A method of measuring the contact angle as set forth in claim 3, further including displacing the interface line between the liquid drop and the plane solid surface in the plane of the solid surface while retaining a constant incidence angle $\alpha$ of the laser beam relative to the plane solid surface in aligning the laser beam with the interface line between the liquid drop and the plane solid surface until the image of the reflected partial beam of the laser beam as reflected by the surface of the liquid drop exhibits a pronounced contrast line on the graduated measuring window.

7. A method of measuring the contact angle as set forth in claim 6, wherein the contact angle r is determined in accordance with the relationship $$r = (90° - \alpha/2) - \delta/2$$

where
- $\alpha$ is the angle of incidence of the laser beam relative to the plane solid surface, and
- $\delta$ is the detected angle between the reflected partial beam of the laser beam as reflected by the surface of the liquid drop and the plane solid surface.

* * * * *